(12) United States Patent  
Ochs et al.

(10) Patent No.: US 8,522,796 B2
(45) Date of Patent: *Sep. 3, 2013

(54) COATED MULTI-RIBBED DENTAL TAPE

(75) Inventors: Harold D. Ochs, Flemington, NJ (US); Joseph Pannia, Hackettstown, NJ (US)

(73) Assignee: McNeil-PPC, Inc, Skillman, NJ (US)

( * ) Notice: Subject to any disclaimer, the term of this patent is extended or adjusted under 35 U.S.C. 154(b) by 449 days.

This patent is subject to a terminal disclaimer.

(21) Appl. No.: 12/748,723

(22) Filed: Mar. 29, 2010

(65) Prior Publication Data

US 2010/0180912 A1    Jul. 22, 2010

Related U.S. Application Data

(63) Continuation-in-part of application No. 12/184,067, filed on Jul. 31, 2008, now Pat. No. 8,061,371, which is a continuation-in-part of application No. 11/937,025, filed on Nov. 8, 2007.

(51) Int. Cl.
*A61C 15/00* (2006.01)

(52) U.S. Cl.
USPC .......................................... 132/321; 132/239

(58) Field of Classification Search
USPC .......................................... 132/323–327, 329
See application file for complete search history.

(56) References Cited

U.S. PATENT DOCUMENTS

| 2,771,084 | A | * | 11/1956 | Fleming ......................... 132/321 |
| 2,821,202 | A | * | 1/1958 | Davis ............................. 132/329 |
| 3,999,562 | A | * | 12/1976 | Reukauf ......................... 132/329 |
| 4,312,370 | A | * | 1/1982 | Hinge ............................. 132/329 |
| 4,450,849 | A | * | 5/1984 | Cerceo et al. .................. 132/321 |
| 4,646,766 | A |   | 3/1987 | Stallard |
| 4,776,358 | A | * | 10/1988 | Lorch ............................. 132/321 |
| 4,836,226 | A |   | 6/1989 | Wolak |
| 4,941,487 | A |   | 7/1990 | VanBeneden |
| 4,996,056 | A |   | 2/1991 | Blass |
| 4,998,978 | A |   | 3/1991 | Varum |
| 5,098,711 | A | * | 3/1992 | Hill et al. ...................... 424/401 |
| 5,209,251 | A |   | 5/1993 | Curtis et al. |
| 5,226,435 | A |   | 7/1993 | Suhonen et al. |

(Continued)

FOREIGN PATENT DOCUMENTS

| EP | 0832615 A | 4/1998 |
| EP | 2057965 A | 5/2009 |
| WO | WO 98/06350 A | 2/1998 |
| WO | WO 02/15814 A | 2/2002 |

OTHER PUBLICATIONS

Moore et al, "In vitro tooth whitening effect of two medicated chewing gums compared to a whitening gum and saliva", *BMC Oral Health* 2008, 8:23.

(Continued)

*Primary Examiner* — Robyn Doan
*Assistant Examiner* — Brianne Kalach

(57) ABSTRACT

The present invention includes coated monofilament dental tapes for removing plaque and/or food debris from interdental spaces of a mammal, which dental tapes have a core body with an aspect ratio of about 5:1 or greater, a first cleaning surface and a second cleaning surface opposite the first cleaning surface, a plurality of ribs disposed along the length of each cleaning surface, and a coating containing about 0.8 milligram per yard of dental tape or more of an abrasive and about 0.8 milligram per yard dental tape or more of sodium bicarbonate.

12 Claims, 3 Drawing Sheets

(56) References Cited

U.S. PATENT DOCUMENTS

| | | | |
|---|---|---|---|
| 5,293,886 A | 3/1994 | Czapor | |
| 5,320,117 A * | 6/1994 | Lazzara et al. | 132/321 |
| 5,357,989 A | 10/1994 | Gathani | |
| 5,357,990 A | 10/1994 | Suhonen et al. | |
| 5,413,127 A | 5/1995 | Hill | |
| 5,518,012 A * | 5/1996 | Dolan et al. | 132/321 |
| 5,588,452 A | 12/1996 | Peck | |
| 5,657,779 A | 8/1997 | Blass et al. | |
| 5,806,539 A | 9/1998 | Blass et al. | |
| 5,865,197 A | 2/1999 | Bible et al. | |
| 5,875,797 A | 3/1999 | Chiang et al. | |
| 5,908,039 A | 6/1999 | Ochs et al. | |
| 5,967,154 A | 10/1999 | Anderson | |
| 6,003,525 A | 12/1999 | Katz | |
| 6,016,816 A | 1/2000 | Ariagno | |
| 6,029,678 A | 2/2000 | Tsao et al. | |
| 6,039,054 A | 3/2000 | Park et al. | |
| 6,251,410 B1 | 6/2001 | Schiraldi et al. | |
| 6,340,027 B1 | 1/2002 | Hagne et al. | |
| 6,371,133 B1 | 4/2002 | Gant | |
| 6,420,024 B1 | 7/2002 | Perez et al. | |
| 6,453,912 B1 | 9/2002 | Antler | |
| 6,527,996 B2 | 3/2003 | Schiraldi et al. | |
| 6,536,448 B2 | 3/2003 | McDevitt et al. | |
| 6,545,077 B2 * | 4/2003 | Hill et al. | 524/277 |
| 6,575,176 B1 | 6/2003 | Hill et al. | |
| 6,591,844 B2 | 7/2003 | Barlow et al. | |
| 6,604,534 B2 * | 8/2003 | Hill | 132/321 |
| 6,609,527 B2 | 8/2003 | Brown | |
| 6,742,528 B2 | 6/2004 | Dave | |
| 6,884,309 B2 | 4/2005 | Schweigert | |
| 6,907,889 B2 | 6/2005 | Brown | |
| 6,916,880 B2 | 7/2005 | Hill et al. | |
| 7,055,530 B2 | 6/2006 | Husted | |
| 7,093,316 B2 | 8/2006 | Chen | |
| 7,281,541 B2 | 10/2007 | Lorch | |
| 2002/0078973 A1 * | 6/2002 | Marwah et al. | 132/321 |
| 2002/0081550 A1 | 6/2002 | Karazivan | |
| 2002/0104548 A1 | 8/2002 | Bhupendra | |
| 2003/0041873 A1 | 3/2003 | Contratto | |
| 2003/0230319 A1 | 12/2003 | Marcon et al. | |
| 2004/0063833 A1 | 4/2004 | Chen | |
| 2005/0071938 A1 | 4/2005 | McDevitt et al. | |
| 2005/0133654 A1 | 6/2005 | Metzger | |
| 2006/0016457 A1 | 1/2006 | Hoffman, III | |
| 2006/0112968 A1 | 6/2006 | Brown et al. | |
| 2006/0237028 A1 * | 10/2006 | Hamidy | 132/321 |
| 2006/0243297 A1 | 11/2006 | Brown | |
| 2009/0120454 A1 | 5/2009 | Ochs et al. | |

OTHER PUBLICATIONS

Yankell et al., "Laboratory Evaluations of Three Dentifrices with Polishing or Brushing", Journal of Clinical Dentistry, vol. 9, issue 3, pp. 61-63 (1998).

* cited by examiner

COATED MULTI-RIBBED DENTAL TAPE

This application is a continuation-in-part application of U.S. patent application Ser. No. 12/184,067, filed Jul. 31, 2008, now U.S. Pat. No. 8,061,371 which is a continuation-in-part application of U.S. patent application Ser. No. 11/937,025, filed Nov. 8, 2007, the contents which are hereby incorporated by reference as if fully set forth herein.

FIELD OF THE INVENTION

The present invention is directed to coated multi-ribbed dental tapes for the removal of food particles or debris and plaque from interstices between the teeth.

BACKGROUND OF THE INVENTION

Dental floss has been in use for more than 100 years for removing plaque and entrapped food particles from between teeth, as well as providing a clean feeling in the mouth. The original floss consisted of twisted silk placed in a jar. Since then, many improvements have been made to dental floss to make flossing more convenient and less problematic. Most improvements have been aimed at solving the negative aspects of flossing. These include reducing fraying and breakage, providing easier insertion between teeth and providing a softer, more gum and hand friendly floss. With the invention of nylon, a high tenacity fray-resistant yarn was used to replace the silk, providing more fray resistance. The addition of wax to twisted multifilament yarn helped anchor fibers together, while providing a lubricious coating for easier insertion. Similarly, the use of air-entangled fibers in combination with wax (see U.S. Pat. No. 5,908,039) provided a softer, more fray-resistant, and better cleaning multifilament floss. Low friction monofilament PTFE yarn coated with wax (see U.S. Pat. No. 5,518,012) provides good ease of insertion, depending upon the thickness and lack of twists or folds, as well as improved fray resistance. Unfortunately, PTFE monofilaments do not clean well, nor do they easily remove food particles from the space between teeth due to the low coefficient of friction of PTFE.

Improvement in the cleaning and particle removal characteristics was attempted by providing a pseudo monofilament product by encasing multifilaments in a soft polymer, (see U.S. Pat. No. 6,039,054 and U.S. Pat. No. 6,742,528). Such flosses slide easily between teeth, provide improved resistance to the PTFE products. Further improvements to flosses were attempted by providing monofilament tapes made of elastomeric materials which neck down when passing into the interdental space and then expand upon relieving tension. A low stretch variety is taught in U.S. Pat. No. 6,591,844. While this monofilament tape exhibits a higher elongation range than commercial floss, it is inferior in softness and mouth feel and fails to provide improved cleaning. A very soft "gel" floss is taught in U.S. Pat. No. 6,029,678, where the yarn is capable of being stretched to at least 200% of its original length, and as much as 2,000% of its original length. In tape form, this floss is at least 0.010 to 0.100-inch thick and more usually from 0.020 to 0.200-inch thick. This means that, while soft, the user will have to apply significant stretch to the product to make it pass between teeth. Once placed in the interdental cavity, this floss will expand and fill the interdental cavity. However, this floss has a smooth surface and is unlikely to remove much plaque or stuck food particles. With this degree of elongation, the consumer may find it difficult to maintain the necessary tension to move the floss up and down during the cleaning process.

Over the years, many improvements have been made to dental floss to make flossing more convenient and less problematic. However, each improvement is typically counterbalanced with a negative effect. Consumer-use tests and clinical studies have shown the monofilament flosses slide better with less fraying, while multifilament products clean better and remove more plaque, but are subject to fraying and breaking. The present invention provides a monofilament tape that not only cleans and whitens better than conventional monofilament flosses, but maintains the positive characteristics of monofilament flosses that make them desirable to consumers, such as mouth feel, easy slide between teeth and resistance to fraying or shredding.

SUMMARY OF THE INVENTION

The present invention is directed to coated monofilament dental tapes for removing plaque and/or food debris from interdental spaces of a mammal, which tapes include a core body having an aspect ratio of about 5:1 or greater, a first cleaning surface and a second cleaning surface opposite the first cleaning surface, where each of the first and second cleaning surfaces includes a plurality of ribs disposed along the length thereof, and where the ratio of the width of the dental tape to the thickness of the dental tape is from about 3:1 to about 25:1. The dental tapes comprise a substantially uniform coating comprising about 0.8 milligram per yard dental tape or more of an abrasive selected from the group consisting of silica, di-calcium phosphate and alumina, and about 0.8 milligram per yard or more of sodium bicarbonate.

DETAILED DESCRIPTION OF THE INVENTION

The dental tapes of the present invention are in the form of a single monofilament. As used herein, the terms "tape", "yarn" and "floss" are interchangeable. The monofilament dental tapes according to the present invention comprise a core body having first and second opposing cleaning surfaces, where at least one of the cleaning surfaces comprise a plurality of ribs disposed along the length thereof. As used herein, the term "rib" means a structural element integral with and protruding from the core body of the dental tape, which element has a configuration and dimension effective to provide for removal of plaque and/or food debris from interdental spaces of a mammal. Ribs may protrude substantially perpendicularly from the core body of the dental tape or at an angle. As used herein, the term "cleaning surface" means that surface of the dental tape that contacts the surface of the tooth when placed within the interdental space of the mammal, thereby providing for removal of plaque and/or food debris from the interdental space. The monofilament dental tape provides the tensile strength and base structure required for good dental floss properties. The dental tape can be made using commercially available material and known monofilament melt extrusion technology and equipment, it does not fray or break, is easy to hold, and readily accepts coatings.

Optionally, the dental tape is made using a material that provides a high degree of compressibility when extruded in the cross-sectional configurations of this invention, allowing it to slip through the tight spaces between teeth. Once in the cavity between teeth and into the interdental space, the dental tape substantially recovers from compression, providing cleaning surfaces containing ribs that act as scrapers to remove plaque and food particles from between the teeth.

Figure 1:
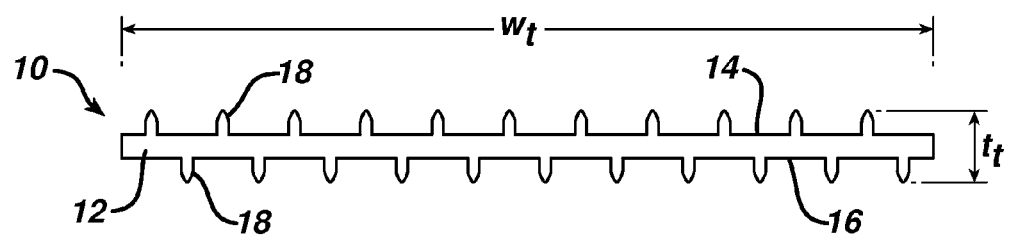
FIG. 1 is a cross-sectional view of one embodiment of a dental tape that may be used in the present invention.
Figure 2:
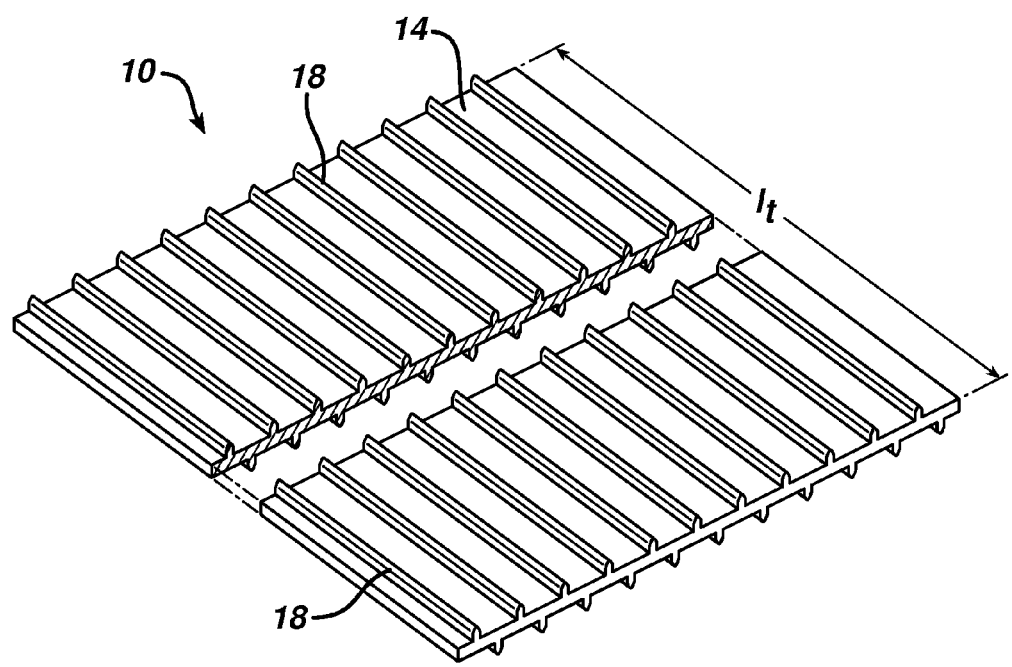
FIG. 2 is a perspective view of FIG. 1 looking from the top and front.
Figure 3:
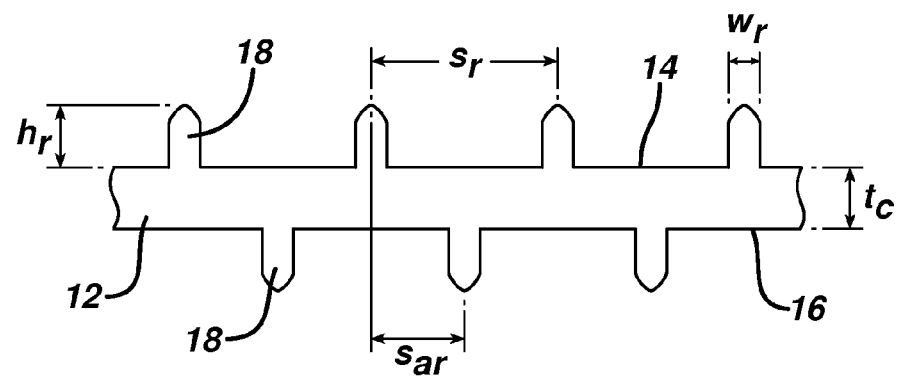
FIG. 3 is an enlarged cross-sectional view of the FIG. 1.

Turning to the drawings, exemplary monofilament dental tape 10 is illustrated in FIGS. 1-3. FIG. 1 shows a cross-sectional view of an embodiment of dental tape 10 comprised of core body 12 with first cleaning surface 14 and second cleaning surface 16. In the embodiment presented, ribs 18 protrude from both first cleaning surface 14 and second cleaning surface 16. In other embodiments, ribs may protrude from only one cleaning surface of the monofilament dental tape. The width of dental tape 10 is represented by $w_t$, while the thickness of dental tape 10 is represented by $t_t$.

The embodiment depicted in FIG. 1 shows a total of twenty-two ribs 18 protruding from cleaning surfaces 14 and 16 of monofilament dental tape 10, eleven from cleaning surface 14, and eleven from cleaning surface 16. In other embodiments of the present invention, the total number of ribs protruding from the cleaning surfaces of the dental tape may be about eight or greater, or about twenty or greater. FIG. 1 shows eleven ribs 18 protruding from both first and second cleaning surfaces 14, 16 of monofilament dental tape 10. It is to be understood, however, that in other embodiments, the number of ribs protruding from the first cleaning surface of the dental tape may be the same, about the same, or significantly different than the number of ribs protruding from the second cleaning surface. In some embodiments, all ribs may be disposed along one of the first or second ribs. In addition, though the cross-sectional profile of the monofilament dental tape 10 shown in FIG. 1 is flat, it is to be understood that in other embodiments the dental tape can have other profiles, such as, but not limited to, arch, wave, or zig-zag.

FIG. 2 shows a perspective view of the FIG. 1 embodiments of dental tape 10 with first cleaning surface 14 and ribs 18 as seen from the top front. The length of dental tape 10 is represented by $l_t$. In FIG. 2 ribs 18 are disposed along the entire length ($l_t$) of dental tape 10.

FIG. 3 shows an enlarged cross-sectional view of the FIG. 1 embodiment of dental tape 10. The thickness of core 12 of dental tape 10 is represented by $t_c$. The height and width of ribs 18 are represented by $h_r$ and $w_r$, respectively. FIG. 3 shows an embodiment in which all ribs are uniform in height and width. It is to be understood that rib height and width can vary across the cleaning surfaces of the dental tape. For example, in one embodiment, ribs could be shorter and/or thinner at the edges of the cleaning surfaces than at the center of the cleaning surfaces.

The spacing between neighboring ribs 18 on first or second cleaning surface 14, 16 of dental tape 10 is represented by $s_r$. In FIG. 3, $s_r$ is depicted as the spacing between neighboring ribs 18 on first cleaning surface 14 of dental tape 10. However, it is to be understood that $s_r$ could be used to measure the spacing between neighboring ribs 18 on either the first or second cleaning surfaces 14, 16 of dental tape 10. FIG. 3 shows an embodiment in which the spacing ($s_r$) between neighboring ribs 18 on cleaning surfaces 14, 16 of dental tape 10 are about equal for all ribs 18. However, it is to be understood that the spacing between neighboring ribs on either cleaning surface of the dental tape do not have to be about equal. So, for example, the spacing between the first two neighboring ribs could be represented as $s_{r1\text{-}2}$, while the spacing between the next two neighboring ribs could be represented as $s_{r2\text{-}3}$, etc. It is envisioned that in other alternative embodiments of the present invention, the spacing between some sets of neighboring ribs could be about equal, while the spacing between other sets of neighboring ribs are not about equal.

Figure 4:
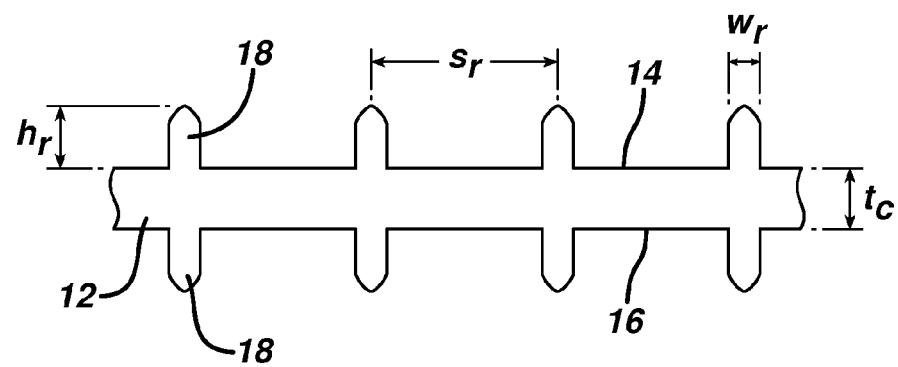
FIG. 4 is an enlarged cross-sectional view of another embodiment of a dental tape that may be used in the present invention.

The term $s_{ar}$ is used to show the spacing between alternating ribs, that is, the spacing between a rib 18 on first cleaning surface 14 and an adjacent rib 18 on second cleaning surface 16 of dental tape 10. FIG. 3 shows an embodiment in which spacing between alternating ribs $s_{ar}$ is about one-half the spacing between neighboring ribs $s_r$. So, the ribs on second cleaning surface 16 of dental tape 10 are offset such that they are positioned about midway between those on first cleaning surface 14. FIG. 4 shows an embodiment in which spacing between alternating ribs $s_{ar}$ is equal to the spacing between neighboring ribs $s_r$. So, the ribs on second cleaning surface 16 of dental tape 10 are aligned with those on first cleaning surface 14.

In the exemplary monofilament dental tape 10 embodiments illustrated in FIGS. 1-4, the cross-sectional shape of ribs 18 is shown as rectangular with a single rounded tip on the distal end of the rib. It is to be understood that other cross-sectional rib shapes are also contemplated embodiments of monofilament ribbed dental tape of the present invention. The cross-sectional shape of rib 18 may be rectangular with a circular tip on the distal end of the rib. In other embodiments not shown, the tip on the distal end of the rib could be oval or semi-circular. The cross-sectional shapes may be rectangular and triangular, respectively.

It is to be understood that all ribs on a given embodiment of the present invention may be, but are not required to be, of the same cross-sectional shape. A mixture of cross-sectional shapes may be employed as determined by the use of the ribbed monofilament dental tape.

Effective flossing of teeth involves placing dental floss into the interdental space between the teeth and then drawing the floss up against the side of each individual tooth to scrub as much of the tooth surface as possible. The monofilament ribbed dental tape of the present invention is inserted into the interdental space and moved thusly. Due to the configuration and dimensions of the ribs, the ribs act like squeegees to remove and trap/hold plaque and food debris in the spacing between the respective ribs with a higher degree of efficiency than, for example, a tape that does not include such ribs disposed along the length thereof, thus providing improved cleaning of the irregular surfaces of teeth.

The floss must be able to pass between tight teeth, a gap of several thousandths of an inch. It must be sized to fit through the gap, or be made of a material and construction that can compress when passing into the interdental space. The monofilament ribbed dental tape of the present invention is thin in one dimension to allow it to slide between tight teeth. It is wide in the other direction to provide two substantial cleaning surfaces to contact teeth surfaces. In certain embodiments the aspect ratio of the core body will be about 5:1 or greater, or about 10:1 or greater, or even about 35:1 or greater. The ratio of the width of the dental tape to the thickness of the dental tape may range from about 3:1 to about 25:1, or from about 10:1 to about 20:1.

The monofilament ribbed dental tape of the present invention can be made using a number of materials known in the art. These materials can be elastomeric or non-elastomeric.

Some non-elastomeric materials from which the dental tape can be made include nylon or polytetrafluoroethylene (PTFE).

In certain embodiments, the dental tape is made of a material that can compress when passing into the interdental space, and then recover a percentage of its original form upon passing into the interdental space. Accordingly, dental tapes of the present invention provide a percent compression of about 50 percent or greater and a percent recovery of about 40 percent or greater, or in certain embodiments, a percent compression of about 60 percent or greater and a percent recovery of about 60 percent or greater. Also, since teeth surfaces are not regular, the interdental space between the teeth will be irregular, having areas which are more or less open, depending on the structure of the particular adjacent teeth. As such, in certain embodiments, the ribs are flexible relative to the core body such that they easily deflect to allow passage into the interdental space. In order to achieve optimal cleaning, it is desirable to have the ribs substantially recover their original dimensions once the force is removed and regain the majority of their original height once the dental tape is in the larger area of the interdental spacing. In this way, the rib will conform to the tooth cross sectional profile, removing more plaque and food.

In certain embodiments, the dental tape is made using an elastomeric material. Elastomeric materials provide a high degree of compressibility when extruded in the cross-sectional configurations of this invention, allowing it to slip through the tight spaces between teeth. Once in the cavity between teeth and into the interdental space, the dental tape substantially recovers from compression, providing cleaning surfaces that act as scrapers to remove plaque and food particles from between the teeth. Elastomeric materials that may be used to form the dental tape of the present invention include, but are not limited to polyamide-polyether block copolymers sold under the tradename PEBAX (Ato Chimie, Hauts-de-Seine France), such as PEBAX 7033, 5533 MX1205, 4033, 3533, and 2533; polyester-polyether block copolymers and polyester-polyester block copolymers sold under the tradename HYTREL (E.I. du Pont de Nemours & Co., Wilmington, Del.), such as HYTREL 7246, 5556, and 4056; aliphatic thermoplastic polyurethane elastomers sold under the tradename TECOFLEX (Lubrizol Advanced Materials, Inc., Cleveland Ohio); aromatic thermoplastic polyurethane elastomers sold under the tradename PELLETHANE (Dow Chemical Co., Midland, Mich.); and thermoplastic polyolefin elastomer sold under the name MULTI-FLEX (Dow Chemical Co., Midland, Mich.). A more detailed discussion regarding such elastomeric materials and their use in manufacturing dental tape can be found in U.S. Pat. No. 6,591,844 to Barlow et al. filed Aug. 23, 2001 and U.S. Pat. No. 6,029,678 to Tsao et al. filed Jan. 21, 1998, both of which are herein incorporated by reference in their entirety.

Dimensions of the monofilament ribbed dental tape of the present invention may be as follows. The width of the dental tape, or $w_t$, is about 0.040 to about 0.100 inches, or about 0.070 to about 0.090 inches. The thickness of the dental tape, $t_t$, is about 0.0035 to about 0.012 inches, or about 0.007 to about 0.009 inches. The thickness of the core body of the dental tape, $t_c$, is about 0.001 to about 0.004 inches, or about 0.002 inches. The height of ribs 18, $h_r$, is about 0.0005 to about 0.004 inches, or about 0.002 inches. The width of the ribs, $w_r$, is about 0.0005 to about 0.003 inches, or about 0.0015 inches. The spacing between neighboring ribs on the cleaning surface of the dental tape, $s_r$, will depend on the width of the dental tape, and the number of ribs on the cleaning surface. For the monofilament ribbed dental tape of the present invention, spacing between neighboring ribs on a cleaning surface is about 0.003 to about 0.020 inches, or about 0.005 to about 0.010 inches.

The term s.sub.ar is used to show the spacing between alternating ribs, that is, the spacing between a rib on the first cleaning surface and a rib on the second cleaning surface of the dental tape. For the purposes of this disclosure, the ratio of $s_{ar}$ to $s_r$ defines the special relationship between alternating ribs. That ratio can vary from just greater than 0 when the ribs on the second cleaning surface are slightly out of alignment with those on the first cleaning surface, through 0.5 when the ribs on the second cleaning surface are positioned about midway between those on the first cleaning surface (see FIG. 3), to 1.0 when the ribs on the second cleaning surface are aligned with those on the first cleaning surface (see FIG. 4). In one embodiment of the monofilament ribbed dental tape of the present invention, the ratio of $s_{ar}$ to $s_r$ is about 0.5.

The monofilament ribbed dental tape of the present invention may be produced by commercial melt spinning process. In this process, the resin is fed into an extruder screw where the material is heated, melted and passed on to a melt pump. The melt pump meters the molten material into a die with a desired profile machined into the surface such that the profile is imparted on the molten extrudate as it exits the die. The extrudate passes from the die and is allowed to flow downwards and start the process of solidification. Some necking down is typical at that point. The material passes into a water bath where the solidification of polymer melt to solid tape is complete. The tape then undergoes a drawing process where it is stretched in the heated state and final characteristics are achieved. The final dental tape is wound onto spools. The spools can be placed on winding machines where the dental tape is wound into bobbins and the bobbins are placed into dispensers or, optionally, the spools are placed on coating machines first, where coatings can be applied prior to the winding operation.

Alternatively, the ribbed dental tape of the present invention may be comprised of multiple materials formed by co-extrusion, or lamination via rolling or adhesion processes.

Alternatively, the dental tape of the invention could also be produced from sheets of material. The resin would be extruded through a shaped die of the correct dimensions imparting the shape on the film. The extrudate passes from the die and is allowed to flow downwards and start the process of solidification. Some necking down is typical at this point. The material passes into a water bath where the solidification of polymer melt to solid tape is complete. The film could be slit at this point and drawn to final dimensions or it could be drawn first and then slit.

Coating compositions applied to coated monofilament dental tapes of the present invention must reliably adhere to the surface of the dental tape. The coating composition must have sufficient adherence to keep the coating on the surface of the dental tape during coating, winding, shipping and unwinding of the dental tape.

Coated monofilament dental tapes of the present invention comprise a substantially uniform coating comprising about 0.8 milligrams per yard dental tape or more of an abrasive selected from the group consisting of silica, di-calcium phosphate and alumina, and about 0.8 milligrams per yard dental tape or more of sodium bicarbonate; or about 1.4 milligram per yard dental tape or more of an abrasive selected from the group consisting of silica, di-calcium phosphate and alumina, and about 1.4 milligram per yard or more of sodium bicarbonate; or about 2 milligram per yard dental tape or more of an abrasive selected from the group consisting of silica, di-calcium phosphate and alumina, in particular silica, and about 2 milligram per yard dental tape of sodium bicarbonate. It will be recognized by those skilled in the art, once having the benefit of this disclosure, that other relative amounts of abrasive and sodium bicarbonate may be used within the above guidelines to provide a coated monofilament dental tape according to the present invention.

Suitable insoluble coatings include, but are not limited to, microcrystalline wax, beeswax, paraffin waxes, low molecular weight polyethylenes, silicone oils, essential oils, and mineral oil. Typically, the insoluble wax coatings have melting temperatures ranging from about 25° C. to about 100° C., optionally from about 35° C. to about 80° C. The waxes may be combined with water insoluble colorants that are FD&C approved for use in the mouth. Suitable colorants include, but are not limited to, synthetically derived colorants such as FD&C Blue #1 Lake, FD&C Blue #2 Lake, FD&C Red #40 Lake, Erythrosin Lake, Amaranth Lake, Ponceau 4R Lake, Carmoisosine Lake, Carmine Lake and colorants generated by converting a naturally derived dye to an aluminum or calcium based salt. Natural colorants such as titanium dioxide and the like may also be used.

The coating composition applied to the dental tape may be a soluble coating, i.e., the coating is such that it tends to dissolve or disperse in saliva present in the oral cavity. Such soluble coatings include soluble waxes or the like, which include, but are not limited to, low molecular weight polyethylene glycols ("PEGs"), such as PEG 1000 and PEG 1450. Combinations of higher molecular weight PEGs and lower molecular weight PEGs, such as a mixture of PEG 3350 and PEG 1000 may be used. Blends of liquid PEG's with high molecular weight PEG's may also be used.

Other coatings include meltable surfactants such as Polyoxamer 407; sialagogues; olfactory stimulants; sensates; essential oils; actives, such as fluoride; cetyl pyridinim chloride (CPC); tetra sodium pyrophosphate; whitening agents other than sodium bicarbonate (baking soda), such as calcium peroxide, hydrogen peroxide, carbamide peroxide and other peroxide compounds capable of generating hydrogen peroxide in-situ; antimicrobials; anti-virals and mixtures thereof.

Such ingredients may be employed as solids, liquids, particles, gels, or the like, and may be encapsulated in conventional polymeric materials by conventional encapsulation techniques to form encapsulated materials having a polymeric shell and a core comprising the ingredient in one of the noted forms, as the case may be. Such ingredients also may be applied directly to the dental tapes of the present invention without the need for a coating carrier, where appropriate.

A coating comprising an insoluble wax may be applied, wherein the coating contains encapsulated components such as spray dried flavors, essential oils, or other ingredients protected and released from soluble spheres within the insoluble wax, or a soluble coating may be applied directly to the yarn or over the insoluble coating. The soluble coating may contain ingredients that are placed directly in the wax or through the use of spray dried or other encapsulation technologies commonly practiced within the art.

In certain embodiments, two insoluble coatings are applied to the dental tape. In these embodiments, the second coating composition must have a lower melting point than the first coating composition.

A soluble coating can be used by itself or as a second coating over an insoluble coating. One or both coatings can contain colorants, flavors, sweeteners, abrasives, anti-tartar agents, actives, such as fluoride salts, and like additives known in the art.

Additional components can be added to coatings for various benefits. These include flavor systems, such as spray dried flavors, flavor enhancers, and sweeteners, such as sodium saccharin. The amount of flavor added typically ranges from 10 percent to 25 percent, based on the total weight of the coating composition. The amount of sweetener typically ranges from 0.1 percent to 1 percent, based on the total weight is of the coating composition.

In formulating a coating, it is desirable to limit the amount of solid additives in the coating composition below about 30% by weight. Coating a dental tape with a coating composition having a solid additive content above this amount may cause difficulty in achieving uniformity of coating and reduce the ability of the coating to adhere to the tape surface. Coatings containing high amounts of solid additives may tend to flake off during processing and during use of the final product.

The dental tape coating may be anhydrous or hydrous. When the coating is hydrous, the water is evaporated upon drying.

The coating may be applied as an add-on typically ranging from about 10 percent to about 60 percent, optionally from about 20 percent to about 50 percent, based on the weight of the fiber substrate.

In certain embodiments, the dental tape is manufactured using equipment and processes capable of doing the following:
1. Feeding monofilament tapes made of elastomeric materials to a coating die at a controlled speed and tension so as to avoid telescoping issues,
2. Pumping the coating composition in a uniform fashion into the coating die,
3. Uniformly and simultaneously applying the coating composition to both sides of the dental tape, and
4. Providing a sufficient period of time during which the coating composition is substantially undisturbed on the dental tape until it is solidified intact.

Figure 5:
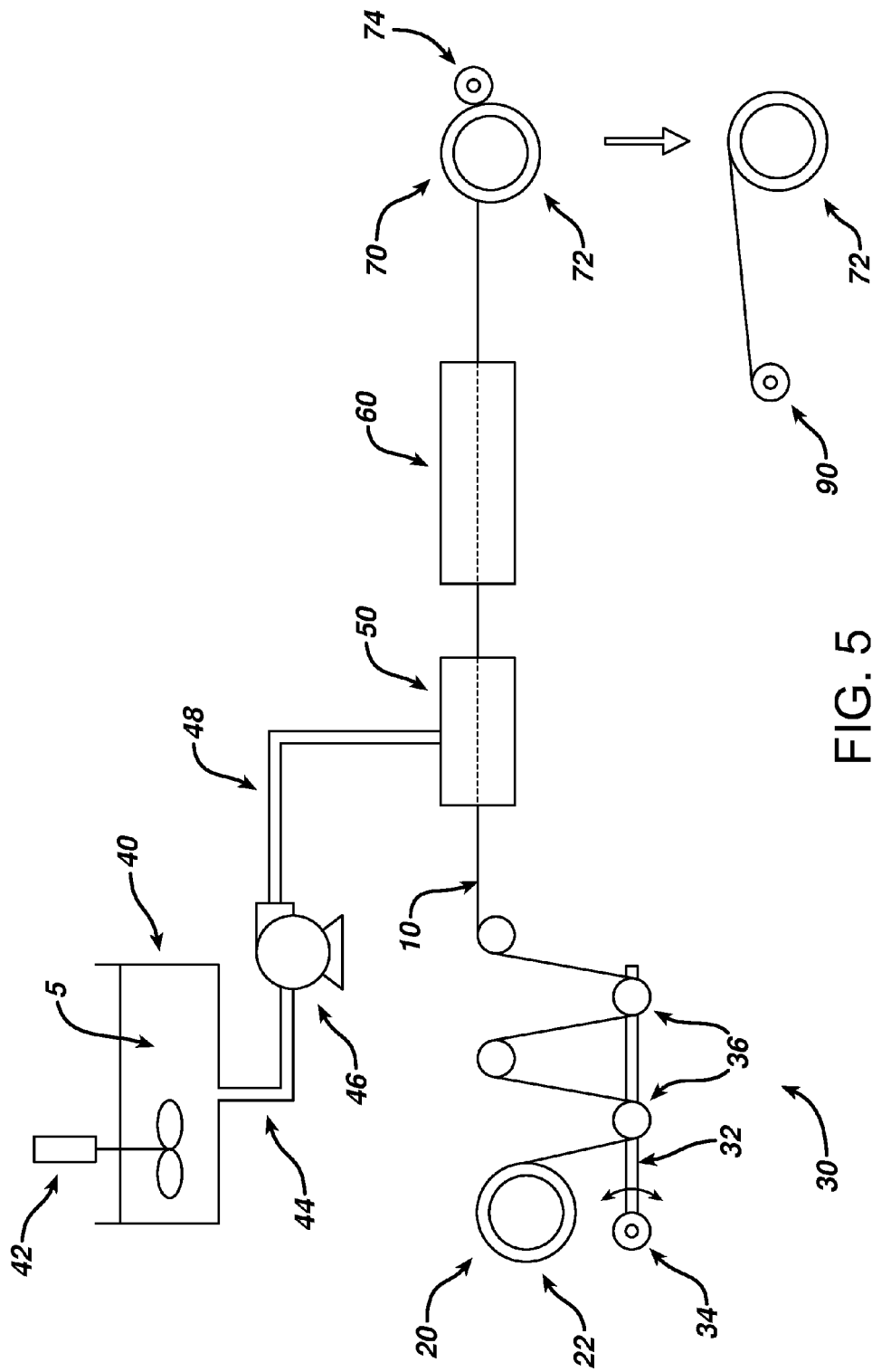
FIG. 5 is a schematic illustration of one embodiment of the manufacturing line for unwinding, coating and rewinding the dental tape of the present invention.

By "uniform" or "substantially uniform," it is meant that, when manually (without the aid of measuring instrumentation) or visually (without the need for magnifying devices beyond corrective eyewear) inspected, the coating should have an even (or relatively or, substantially even) thickness and be free from (or sufficiently [or substantially] free from) defects (such as pinholes or voids) in the coated area. The above-mentioned process for manufacturing the elastomeric monofilament dental tape of the invention is illustrated in FIG. 5. In the first step, the coating composition 5, typically a wax, is liquefied if necessary, as by heating, in a mix tank 40. A high sheer mixer 42, such as a Rotostat High Sheer Mixer Model #XPBL, made by Admix, can be used to keep coating composition 5 homogeneous. Typically, a Rotosolver head blade is used in the high sheer mixer 42 and is operated at, e.g., 1700 rpm.

The coating composition is then allowed to flow from mix tank 40, via a first pipe 44 into a positive displacement pump 46 which, when driven at a given speed, delivers a constant amount of coating, via a second pipe 48, to a coating die 50. The positive displacement pump can be a vane type positive displacement pumps, piston pumps, or similar type pumps. In certain embodiments, a Kerr piston pump, supplied by Kerr Corp., Sulfur, Okla., is used. Piston pumps, generally, facilitate the evenness and uniformity of coatings where the coating composition 5 contains solid particulates such as abrasives. In certain embodiments, positive displacement pumps are used since the passages bores, pipes, channels or outlets used in such embodiments to deliver coating composition 5 are generally positioned or oriented such that the directional path or track of the passage bores, pipes, channels or outlets points upwardly and toward or horizontally level with and toward the position of the dental tape 10 to be coated such that gravity has no effect or minimal effect on the flow of the coating composition from mix tank 40 onto the dental tape 10.

In certain embodiments, the dental tape 10 is simultaneously fed and pulled through the process by a combination of a powered unwinding system 20 and a floss rewinding system 70. The dental tape 10 is fed or unwound at a low tension and, in certain embodiments, pulled perpendicularly from feed spool 22 across or through sensing arm assembly 30. Sensing arm assembly 30 is provided for monitoring the tension of the dental tape 10 as it enters coating die 50. In certain embodiments, the sensing arm assembly 30 has an arm 32, a pivot point 34, and rollers 36 over which the dental tape 10 passes. Sensing arm assembly 30 is used to maintain a substantially constant low feeding or unwinding tension on dental tape 10 by adjusting the speed of power unwinding system 20 as it is simultaneously fed and pulled into the coating process system. In certain embodiments, where the dental tape passes through the coating process at line speed rates greater than about 1000 fpm, or optionally from about 1500 fpm to about 2500 fpm, or optionally from about 2000 fpm, the constant low unwinding tension is generally maintained at from about 50 grams-force to about 100 grams-force, optionally at from about 60 grams-force to about 100 grams-force for dental tape 10 having denier of about 400 to about 1200.

After coating, dental tape 10 is collected on a take-up spool 72. The speed at which take-up spool 72 operates is controlled by an electronic controller system. The controller may be a computer, a programmable logic controller or similar device. In the embodiment shown in FIG. 5, a speed sensing roll 74 rides on surface of the tape on take-up spool 72. Speed sensing roll 74 generates a signal which is fed to an electronic controller, such as a Fenner M-drive. The controller controls the voltage of the motor which drives the speed of take-up spool 72. The use of the signal generated by speed sensing roll 74 in controlling the speed of take-up spool 72 helps to maintain a constant speed or velocity of the dental tape 10 through the coating process, controlling and maintaining the tension on dental tape 10 to less than 250 or (about 250) grams-force. The electronic controller also controls the speed of positive displacement pump 46. Thus the velocity of dental tape 10 is maintained while a constant amount of coating composition 5 is pumped into the coating die 50.

In certain embodiments the coating die 50 contains at least two rollers around which elastomeric dental tape 10 has at least some wrap. In certain embodiments, the number of rollers can range from 2, optionally 3, optionally 4 or greater rollers, or optionally 2 to 7 rollers or, optionally, from 3 to 5 rollers. Generally, dental tape 10 wraps around the rollers at from about 90° to about 270°. The rollers assist in applying coating composition 5 to dental tape 10. Downstream of the rollers there is typically a slot die region where coating composition 5 is smoothed onto the surface of dental tape 10. In certain embodiments, the slot die is in the form of a groove having parallel sides or walls, the groove, optionally, having a radius at its bottom for guiding the dental tape into a slot. In certain embodiments, the slot is sized such that excess coating is removed from dental tape 10 as it passes through the die while, at the same time, minimizing any additional tension on dental tape 10 caused by the slot die as the tape 10 passes through the die. As will be apparent to those skilled in the art, the dimensions of the groove and slot will depend upon such factors as the denier and type of elastomeric monofilament dental tape 10 and the amount of coating composition 5 being applied thereto.

Coating composition 5, once applied to dental tape 10, must be solidified. Solidification can be accomplished by having a cooling area 60. Cooling area 60 can be an open area where coating 5 cools under ambient conditions. Alternatively, cooling area 60 can be a chamber where refrigerated or room air is blown over dental tape 10 to increase the rate of cooling. In order to avoid undesirable discontinuities in coating 5, dental tape 10 should not contact any surfaces until coating 5 has solidified. Once coating 5 is cooled sufficiently to prevent any disruption of the outer surface, it is rewound on floss rewinding system 70. In certain embodiments, spool 72 with dental tape 10 is then removed for later processing into conventional bobbins. A more detailed description of processes and apparatus useful in manufacturing the coated multiribbed dental floss of the present invention may be found in United States Patent Application Publication Number US 2009/0120454 A1, the contents of which is hereby incorporated by reference in its entirety.

EXAMPLES

Dental tapes illustrated in following examples illustrate specific embodiments of dental tapes that may be used in the present invention, but are not intended to be limiting thereof. Other modifications can be undertaken by the skilled artisan without departing from the spirit and scope of this invention.

Example 1

Dental tape that may be used in the present invention was produced using PEBAX MX 1205 resin. The resin was dried for over 3 hours at 75° C., fed into a Haake 20 mm extruder with a Slack and Parr gear melt pump attached and extruded through a shaped die formed of stainless steel, and having a cross-section similar to that of the dental tape shown in FIG. 1. The extruded dental tape included eleven ribs protruding from both the first and second cleaning surfaces. The overall width of the slot ($w_t$) was 0.303 inches. The thickness of the core body of the die ($t_c$) was 0.0035 inches. The height and width of the rib portions of the die ($h_r$ and $w_r$) were 0.0075 inches and 0.0035 inches, respectively. The spacing between neighboring ribs on both cleaning surfaces ($s_r$) was 0.026 inches, and the ratio of $s_{ar}$ to $s_r$ was 0.5, i.e. the ribs on the second cleaning surface were positioned about midway between those on the first cleaning surface.

The extruded tape passed through a room temperature water bath and was wound on a spool.

One extrusion was performed using the shaped die to prepare the dental of the invention. For comparison, two extrusions were performed through a flat die to prepare comparative dental tapes with no ribs. For Run 2, the die thickness and width were 0.085 inches and 0.490 inches, respectively. For Run 3, the die thickness and width were 0.012 inches and 0.350 inches, respectively.

The conditions for the three extrusions are shown on Table I:

TABLE I

Extrusion conditions.

| | Run 1 | Run 2 | Run 3 |
|---|---|---|---|
| Die | shaped | flat | Flat |
| Barrel T (Zones 1-6), ° C. | 195 | 220 | 213 |
| Die T, ° C. | 203 | 233 | 216 |
| Flow rate, cc/min | 4.8 | 4.3 | 6.4 |
| Die to water bath, inches | 1 | 3 | 7 |
| Take-up speed, feet/min | 20 | 24 | 24 |

The tapes from the three extrusion runs were subjected to drawing operations to produce the final dental tapes. In the drawing operation, the tape was unwound from the spool, passed over a heated roller, across a hot plate, and rewound on a second roller. Conditions for the three drawing runs are shown on Table II:

TABLE II

Drawing conditions.

|  | Run 1 | Run 2 | Run 3 |
|---|---|---|---|
| Roll 1 T, ° C. | 60 | 60 | 60 |
| Plate T, ° C. | 100 | 90 | 60 |
| Roll 1 Speed, meter/min | 2 | 2 | 2 |
| Roll 2 Speed, meter/min | 18 | 14 | 12 |
| Draw ratio | 9 to 1 | 7 to 1 | 6 to 1 |

The overall width, thickness, and denier of the tapes were measured and are summarized on Table III:

TABLE III

Tape dimensions.

|  | Run 1 | Run 2 | Run 3 |
|---|---|---|---|
| Width, inches | 0.075 | 0.073 | 0.072 |
| Thickness, inches | 0.005 | 0.005 | 0.002 |
| Denier | 1008 | 1586 | 861 |

The compression and recovery expansion of the tapes made above were measured using an apparatus comprised of 2 steel shafts that are used to simulate two adjacent teeth surfaces. One of the steel shafts was stationary, while the other shaft pivoted. A thickness indicator was set to zero when the moving shaft was resting on the fixed shaft. The tape was placed at a ninety-degree angle to the axis of the stationary shaft. The moveable shaft, constructed so as to exert little pressure on the nip point, was allowed to rest on top of the tape, and the original thickness ($t_o$) reading was taken from the indicator. Next, a one-pound weight was applied directly above the nip point, and the compressed thickness ($t_c$) reading was recorded. The percent compression was calculated as Percent Compression=$100 \times (t_o - t_c)/t_o$ A measure of the recovery expansion of the tape was obtained using this device by removing all force and noting the recovery thickness ($t_r$) reading on the indicator. The percent recovery was calculated as:

Percent Recovery=$100 \times (t_r - t_c)/(t_o - t_c)$

The percent compression and percent recovery of each of the tapes were measured, and the results are summarized on Table IV:

TABLE IV

Tape compression and recovery.

|  | Run 1 | Run 2 | Run 3 |
|---|---|---|---|
| Original Thickness, inches | 0.005 | 0.005 | 0.002 |
| Compression, % | 70 | 31 | 25 |
| Recovery, % | 67 | 93 | 100 |

Next, the tensile properties and tenacity of the tapes were measured using an Instron universal testing machine with a specimen length of 10 inches, and a cross-head speed of 10 inches per minute.

The tensile strength, percent elongation at break and tenacity of each of the tapes were measured, and the results are summarized on Table V:

TABLE V

Tape tensile properties.

|  | Run 1 | Run 2 | Run 3 |
|---|---|---|---|
| Tensile strength, lbs | 7.5 | 9.8 | 6.5 |
| Elongation at Break, % | 64 | 87 | 52 |
| Tenacity, grams/denier | 3.7 | 2.8 | 3.1 |

Example 2

Dental tape that may be used in the present invention was produced using several other resins. The resins used are listed on Table VI.

TABLE VI

|  | Resin |
|---|---|
| Run 4 | HYTREL 4056 |
| Run 5 | HYTREL 4056 |
| Run 6 | PELLETHANE 2363-90AE |
| Run 7 | MULTIFLEX 1047S |
| Run 8 | TECOFLEX EG-100A |

The resins were dried for over 3 hours at 75° C. They were processed in the extruder of Example 1, using the ribbed die described in Example 1.

The conditions for the extrusions are shown on Table VII:

TABLE VII

Extrusion conditions.

|  | Run 4 | Run 5 | Run 6 | Run 7 | Run 8 |
|---|---|---|---|---|---|
| Barrel T (Zones 1-6), ° C. | 230 | 225 | 200 | 260 | 187 |
| Die T, ° C. | 239 | 235 | 202 | 262 | 189 |
| Flow rate, cc/min | NA | NA | 3.2 | 4.3 | 3.2 |
| Die to water bath, inches | 1 | 4 | 2.5 | 8 | 4 |
| Take-up speed, feet/min | 20 | 20 | 20 | 14 | 17 |

The tapes from the extrusion runs were drawn following the procedure of Example 1. Conditions for the three drawing runs are shown on Table VIII:

TABLE VIII

Drawing conditions.

|  | Run 4 | Run 5 | Run 6 | Run 7 | Run 8 |
|---|---|---|---|---|---|
| Roll 1 T, ° C. | cold | cold | 50 | 55 | 70 |
| Plate T, ° C. | 100 | 100 | 90 | 115 | 70 |
| Roll 1 Speed, meter/min | 2 | 2 | 2 | 2 | 2 |
| Roll 2 Speed, meter/min | 16 | 15 | 14 | 12 | 16 |
| Draw Ratio | 8 to 1 | 7.5 to 1 | 7 to 1 | 6 to 1 | 8 to 1 |

The overall width, thickness, and denier of the tapes were measured, and are summarized on Table IX:

TABLE IX

Tape dimensions.

|  | Run 4 | Run 5 | Run 6 | Run 7 | Run 8 |
|---|---|---|---|---|---|
| Width, inches | 0.080 | 0.080 | 0.090 | 0.070 | 0.060 |
| Thickness, inches | 0.0065 | 0.0065 | 0.0065 | 0.007 | 0.0045 |

The tensile properties of the tapes were measured as described in Example 1. The tensile strength and percent elongation at break are summarized on Table X:

TABLE X

Tape tensile properties.

|  | Run 4 | Run 5 | Run 6 | Run 7 | Run 8 |
|---|---|---|---|---|---|
| Tensile strength, lbs | 9.5 | 8.7 | 7.6 | 3.1 | 3.5 |
| St. Dev. | 0.3 | 0.6 | 0.4 | 0.2 | 0.4 |
| Elongation at Break, % | 102 | 87 | 105 | 25 | 68 |
| St. Dev. | 4 | 5 | 10 | 6 | 6 |

Example 3

Dental tape that may be used in the present invention was produced using PEBAX MX 1205 resin where the drawing conditions were modified to change the dimensions of the final tape. The resins were dried for over 3 hours at 75° C., and processed in the extruder of Example 1, using the ribbed die described in Example 1.

The conditions for the extrusions are shown on Table XI:

TABLE XI

Extrusion conditions.

|  | Run 9 | Run 10 | Run 11 |
|---|---|---|---|
| Barrel T (Zones 1-6), ° C. | 205 | 195 | 210 |
| Die T, ° C. | 207 | 197 | 212 |
| Flow rate, cc/min | 3.2 | 3.2 | 3.2 |
| Die to water bath, inches | 6 | 2 | 1.5 |
| Take-up speed, feet/min | 22 | 22 | 22 |

The tapes from the extrusion runs were drawn following the procedure of Example 1. Conditions for the three drawing runs are shown on Table XII:

TABLE XII

Drawing conditions.

|  | Run 9 | Run 10 | Run 11 |
|---|---|---|---|
| Roll 1 T, ° C. | cold | cold | 50 |
| Plate T, ° C. | 80 | 80 | 80 |
| Roll 1 Speed, meter/min | 2 | 2 | 2 |
| Roll 2 Speed, meter/min | 18 | 18 | 18 |
| Draw Ratio | 9 to 1 | 9 to 1 | 9 to 1 |

The overall width, thickness, and denier of the tapes were measured, and are summarized on Table XIII:

TABLE XIII

Tape dimensions.

|  | Run 9 | Run 10 | Run 11 |
|---|---|---|---|
| Width, inches | 0.055 | 0.055 | 0.060 |
| Thickness, inches | 0.0035 | 0.0035 | 0.0045 |

The tensile properties of the tapes were measured as described in Example 1. The tensile strength and percent elongation at break are summarized on Table XIV:

TABLE XIV

Tape tensile properties.

|  | Run 9 | Run 10 | Run 11 |
|---|---|---|---|
| Tensile strength, lbs | 6.4 | 6.6 | 5.0 |
| St. Dev. | 0.1 | 0.5 | 0.5 |
| Elongation at Break, % | 37 | 34 | 138 |
| St. Dev. | 4 | 6 | 10 |

Example 4

Dental tape that may be used in the present invention was produced using PEBAX MX 1205, 3533, and 2533 resins. The resins were dried for over 3 hours at 75° C., and processed in the extruder of Example 1, using the ribbed die described in Example 1.

The conditions for the extrusions are shown on Table XV:

TABLE XV

Extrusion conditions.

|  | Run 1 | Run 12 | Run 13 |
|---|---|---|---|
| PEBAX Resin | MX 1205 | 3533 | 2533 |
| Barrel T (Zones 1-6), ° C. | 195 | 220 | 200 |
| Die T, ° C. | 203 | 222 | 202 |
| Flow rate, cc/min | 4.8 | 4.8 | 4.8 |
| Die to water bath, inches | 1 | 4 | 3 |
| Take-up speed, feet/min | 20 | 17 | 18 |

The tapes from the extrusion runs were drawn following the procedure of Example 1. Conditions for the three drawing runs are shown on Table XVI:

TABLE XVI

Drawing conditions.

|  | Run 1 | Run 12 | Run 13 |
|---|---|---|---|
| Roll 1 T, ° C. | 60 | 60 | 70 |
| Plate T, ° C. | 100 | 100 | 85 |
| Roll 1 Speed, meter/min | 2 | 1 | 2 |
| Roll 2 Speed, meter/min | 18 | 9 | 17 |
| Draw Ratio | 9 to 1 | 9 to 1 | 8.5 to 1 |

The overall width, thickness, and denier of the tapes were measured, and are summarized on Table XVII:

TABLE XVII

Tape dimensions.

| | Run 1 | Run 12 | Run 13 |
|---|---|---|---|
| Width, inches | 0.075 | 0.080 | 0.080 |
| Thickness, inches | 0.005 | 0.0055 | 0.005 |

The tensile properties of the tapes were measured as described in Example 1. The tensile strength and percent elongation at break are summarized on Table XVIII:

TABLE XVIII

Tape tensile properties.

| | Run 1 | Run 12 | Run 13 |
|---|---|---|---|
| Tensile strength, lbs | 7.5 | 6.1 | 4.8 |
| Elongation at Break, % | 64 | 142 | 194 |

Example 5

Dental tape that may be used in the present invention was produced using PEBAX MX 1205 resin where the number of ribs was modified to change the structure of the final tape.

The die was formed of stainless steel, and had a cross-section similar to that in Example 1. The difference is that in Example 1, there were eleven ribs protruding from both the first and second cleaning surfaces. Here, there were five ribs protruding from both the first and second cleaning surfaces. The overall width of the slot, or $w_t$, was 0.305 inches. The thickness of the core body of the die $t_r$ was 0.0035 inches. The height and width of the rib portions of the die ($h_r$ and $w_r$, respectively) were 0.0075 inches and 0.0035 inches. The spacing between neighboring ribs both cleaning surfaces was ($s_r$) is 0.050 inches, and the ratio of $s_{ar}$ to $s_r$ is 0.5, i.e. the ribs on second cleaning surface were positioned about midway between those on first cleaning surface.

The resin was dried for over 3 hours at 75° C., and processed in the extruder of Example 1. The conditions for the extrusions are shown on Table XIX:

TABLE XIX

Extrusion conditions.

| | Run 1 | Run 14 |
|---|---|---|
| Number of Ribs | 22 | 10 |
| Barrel T (Zones 1-6), ° C. | 195 | 195 |
| Die T, ° C. | 203 | 196 |
| Flow rate, cc/min | 4.8 | 4.3 |
| Die to water bath, inches | 1 | 2 |
| Take-up speed, feet/min | 20 | 23 |

The tapes from the extrusion runs were drawn following the procedure of Example 1. Conditions for the three drawing runs are shown on Table XX:

TABLE XX

Drawing conditions.

| | Run 1 | Run 14 |
|---|---|---|
| Roll 1 T, ° C. | 60 | Cold |
| Plate T, ° C. | 100 | 80 |
| Roll 1 Speed, meter/min | 2 | 2 |
| Roll 2 Speed, meter/min | 18 | 17 |
| Draw Ratio | 9 to 1 | 8.5 to 1 |

Example 6

Dental tape that may be used in the present invention was produced using PEBAX MX 1205 resin where the width of ribs was modified to change the structure and dimensions of the final tape.

The die was formed of stainless steel, and had a cross-section similar to that in Example 1. There were eleven ribs protruding from both the first and second cleaning surfaces. The overall width of the slot, or $w_t$, was 0.303 inches. The thickness of the core body of the die $t_c$ was 0.0035 inches. The height and width of rib portions of the die ($h_r$ and $w_r$, respectively) were 0.0075 inches and 0.0025 inches. In Example 1, the width of rib portions of the die ($w_r$) was 0.0035 inches. The spacing between neighboring ribs both cleaning surfaces is ($s_r$) was 0.026 inches, and the ratio of $s_{ar}$ to $s_r$ was 0.5, i.e. the ribs on second cleaning surface were positioned about midway between those on first cleaning surface.

The resin was dried for over 3 hours at 75° C., and processed in the extruder of Example 1. The conditions for the extrusions are shown on Table XXI:

TABLE XXI

Extrusion conditions.

| | Run 1 | Run 15 |
|---|---|---|
| Width of Ribs, inches | 0.0035 | 0.0025 |
| Barrel T (Zones 1-6), ° C. | 195 | 193 |
| Die T, ° C. | 203 | 193 |
| Flow rate, cc/min | 4.8 | 4.3 |
| Die to water bath, inches | 1 | 2 |
| Takeup speed, feet/min | 20 | 20 |

The tapes from the extrusion runs were drawn following the procedure of Example 1. Conditions for the three drawing runs are shown on Table XXII:

TABLE XXII

Drawing conditions.

| | Run 1 | Run 14 |
|---|---|---|
| Roll 1 T, ° C. | 60 | Cold |
| Plate T, ° C. | 100 | 85 |
| Roll 1 Speed, meter/min | 2 | 2 |
| Roll 2 Speed, meter/min | 18 | 18 |
| Draw Ratio | 9 to 1 | 9 to 1 |

Example 7

Dental tape that may be used in the present invention was produced using PEBAX MX 1205 resin where the height of the ribs was modified to change the structure and dimensions of the final tape.

The die was formed of stainless steel, and had a cross-section similar to that in Example 1. There were eleven ribs protruding from both the first and second cleaning surfaces. The overall width of the slot, or $w_t$, was 0.303 inches. The thickness of the core body of the die $t_c$ was 0.0035 inches. The height and width of the rib portions of the die ($h_r$ and $w_r$, respectively) were 0.0038 inches and 0.0035 inches. In Example 1, the height of rib portions of the die ($h_r$) was 0.0075 inches. The spacing between neighboring ribs both cleaning surfaces is ($s_r$) was 0.026 inches, and the ratio of $s_{ar}$ to $s_r$ was 0.5, i.e. the ribs on second cleaning surface were positioned about midway between those on first cleaning surface.

The resin was dried for over 3 hours at 75° C., and processed in the extruder of Example 1. The conditions for the extrusions are shown on Table XXIII:

TABLE XXIII

Extrusion conditions.

|  | Run 1 | Run 16 |
| --- | --- | --- |
| Height of Ribs, inches | 0.0075 | 0.0038 |
| Barrel T (Zones 1-6), ° C. | 195 | 197 |
| Die T, ° C. | 203 | 199 |
| Flow rate, cc/min | 4.8 | 4.3 |
| Die to water bath, inches | 1 | 2 |
| Take-up speed, feet/min | 20 | 20 |

The tapes from the extrusion runs were drawn following the procedure of Example 1. Conditions for the three drawing runs are shown on Table XXIV:

TABLE XXIV

Drawing conditions.

|  | Run 1 | Run 14 |
| --- | --- | --- |
| Roll 1 T, ° C. | 60 | Cold |
| Plate T, ° C. | 100 | 85 |
| Roll 1 Speed, meter/min | 2 | 2 |
| Roll 2 Speed, meter/min | 18 | 18 |
| Draw Ratio | 9 to 1 | 9 to 1 |

Example 8

Dental tape spool rolls were formed in accordance with the coating and winding processes described herein and using the component sizes and/or type described below and summarized in Table XXV.

TABLE XXV

| Component | Type/Size |
| --- | --- |
| Pulley 82e | 14 Teeth |
| Pulley 82d | 17 Teeth |
| Pulley 82c | 19 Teeth |
| Pulley 82f | 14 Teeth |
| Pulley 82g | 16 Teeth |
| Pulley 82h | 20 Teeth |
| Traversing Cam | 11.5 inches, 6 turns |
| Guide Traverse | end to end cam |

Ordering the above pulley sizes sequentially (e.g., 82e is connected to 82d which is connected 82c etc. as shown in FIG. 8) and determining the product of the ratios of the sizes of the sequentially ordered pulleys or Ratio A (as shown in I below)

$$\text{Ratio } A = P_1/P_2 \times P_3/P_4 \times P_{Z-1}/P_Z \qquad \text{I}$$

Where $P_1$ to $P_z$ are the sizes of the pulleys sequentially ordered from spool 72 and to the traverse barrel cam 86 of rewinding system 70, results in the following ratio:

$$\text{Ratio } A = (\text{Pulley } 82e/\text{Pulley } 82d) \times (\text{Pulley } 82c/\text{Pulley } 82f) \times (\text{Pulley } 82g/\text{Pulley } 82h) = (14/17) \times (19/14) \times (16/20) = 0.8941$$

A traverse barrel cam was selected to provide a traversing cam guide traverse of 11.5 inches end to end for every 6 revolutions of traverse barrel cam 86. This results in a cam advance equal to the following:

$$\text{Cam Advance} = \text{Traversing Cam Guide Traverse}/$$
$$6 \text{ Revolutions of Traverse Barrel Cam}$$
$$= 11.5/6 = 1.9166 \text{ inches per Traverse}$$
$$\text{Barrel Cam revolution}$$

Ratio A indicates that for each revolution of the spool 72, the traverse barrel cam travels 0.8941 of the spool revolution. This results in the following travel distance for the traversing cam guide 76 per revolution of spool 72:

$$\text{Travel Distance of traversing cam guide per revolution of spool} = \text{Cam Pulley Ratio} \times \text{Cam Advance}$$
$$= 0.8941 \cdot \text{times} \cdot 1.9166 = 1.71 \text{ inches}$$
$$\text{per spool revolution}$$

The core diameter $d_s$ of spool 72 was measured to be 6.21 inches, therefore, the distance traveled by any point on the outer surface of the core of spool 72 after one revolution of spool 72 or circumference C can be calculated as follows:

$$\text{Circumference } C = 6.21 \text{ inches} \times \pi = (6.21) 3.1411 = 19.5 \text{ inches}$$

The helix angle θ (the angle formed by a strand of dental tape and plane rΦ of the spool which is perpendicular to the longitudinal axis z of the spool 72 as shown in FIG. 25) formed by dental tape 10 as it is initially wound around the core of spool 72 can then be calculated as follows:

$$\text{Travel Distance of traversing cam guide per spool revolution}/\text{Circumference } C = 1.71/19.5$$

$$1.71/19.5 = 0.0876 = \sin^{-1} \theta (\text{Helix Angle})$$

Where Helix Angle θ'=5.03°

As will be understood by the skilled artisan, as the spool 72 roll grows, the helix angle θ decreases. For example, as one inch of dental tape is wound onto the core of spool 72, helix angle decreases. This is exemplified as follows:

The diameter of spool after 1 adding one inch layer of tape=6.21 inches+2 inches (1 inch of added layer results in diameter increasing by 2 inches)=8.21 inches, hence:

$$\text{Circumference of Spool with Tape} = \text{diameter of spool with tape} \times \pi$$
$$= (8.21)3.1411$$
$$= 25.7 \text{ inches, hence}$$

Travel distance of traversing cam guide per spool revolution/Circumference of Spool and Tape=1.71/25.7 inches=0.066=$\sin^{-1}\theta'$(Helix Angle)

Where Helix Angle $\theta'=3.8°$

Therefore, as about an inch of material is wound around the spool, the helix angle chances by about 1° ($\theta-\theta'=5.03°-3.8°=1.5°$).

Example 9

Dental tape spool rolls were formed in accordance with the coating and winding process of Example 8. The coatings comprised microcrystalline wax (Multiwax-W445, Crompton Corp. Petrolia, Pa.), flavor (Virginia Dare, Brooklyn, N.Y.), sodium saccharin (PMC Specialties, Cincinnati, Ohio), baking soda (sodium bicarbonate; Church and Dwight, Old Fort, Ohio), and one of two silicas (Sident 10, Degussa GmbH, Wesseling, Germany or Zeodent, J.M. Huber Corporation, Atlanta, Ga.). The coating add-on % for all samples was approximately 33 w/w %. The yarn used was a 865 denier mutli-ribbed floss made from PEBAX 1205 as previously described. All coating formulations were 17 w/w % flavor, and 1 w/w % sodium saccharin. The remaining w/w % of the coating formulations are shown on Table XXVI.

TABLE XXVI

| | | Coating Formulations | | |
|---|---|---|---|---|
| Formulation | Wax | Baking soda | Sident 10 silica | Zeodent silica |
| 9-1 | 82 | 0 | 0 | 0 |
| 9-2 | 72 | 0 | 10 | 0 |
| 9-3 | 72 | 2.5 | 7.5 | 0 |
| 9-4 | 72 | 5 | 5 | 0 |
| 9-5 | 72 | 5 | 0 | 5 |
| 9-6 | 72 | 7.5 | 2.5 | 0 |
| 9-7 | 72 | 10 | 0 | 0 |
| 9-8 | 75 | 3.5 | 3.5 | 0 |

Dental specimens were prepared and stained following the methods discussed in M. Moore, et al., *BMC Oral Health* 2008, 8:23, and summarized below. Four millimeter squares of dental enamel from bovine permanent incisors, which are a representative model for human teeth, were cut using a diamond cutting disk. Squares of enamel were embedded in clear, self-curing, denture base repair acyric (Patterson Dental Supply, St. Paul, Minn.) to provide a 1.5 cm square block with the tooth enamel labial surface exposed. The enamel surface was then smoothed by hand-sanding and hand-polished to a mirror finish using a water/ceramic slurry. The finished specimens were examined under a dissecting microscope and discarded if surface imperfections were observed.

To make the polished tooth surfaces more similar to natural teeth and promote the formation of stain on the enamel, the specimens were etched for 60 seconds in 0.2 M HCl, followed by a 30 second immersion in a saturated solution of sodium carbonate. A final etch was performed with 1% phytic acid for 60 seconds.

The specimens were then rinsed with deionized water and attached to a staining apparatus, which was designed to provide alternate immersion into the staining broth and air-drying of the specimens. The staining apparatus had a Teflon rod connected to an electric motor. Specimens were attached to the rod so that when the rod was rotated, the specimens were dipped into a trough which held the staining broth.

The staining broth was prepared using 1.02 gm instant coffee, 1.02 gm instant tea, 10 ml red wine, 0.75 gm gastric mucin (Nutritional Biochemicals Corp., Cleveland, Ohio) and 50 ml of a 24-hour *Micrococcus luteus* culture in 250 ml of sterilized trypticase soy broth. The apparatus, containing the attached enamel specimens and staining broth, was then placed in an incubator at 37° C. with the specimens rotating continuously through the staining broth and air. The staining broth was replaced with fresh broth once every 24 hours for ten consecutive days. The trough and specimens were rinsed and brushed with deionized water to remove any loose deposits at each broth change. On the eleventh day, $FeCl_3.6H_2O$ was added to the staining broth. This was continued with daily broth changes until the stain on the specimens was sufficiently dark ($L^*<35$). The specimens were then removed from the staining broth, brushed thoroughly with deionized water, and refrigerated in a humidor until used.

The flossing unit that was used was built internally. Each enamel specimen was vertically positioned in a holder. A strip of floss, placed under ¾-pounds of tension, was wrapped around and through rods that held the floss in place and in contact with the specimen. The unit was activated, and a 5-stroke up/down motion was performed. The first strip of floss was replaced, and the unit activation was repeated. The process was repeated on the same enamel specimen until 150 strokes were performed with 30 strips of floss being tested. Specimens were removed from the flossing unit, and wiped off with alcohol.

Evaluation of stain removal was done by measuring the extrinsic stain on the enamel specimens before and after flossing. The color of the extrinsic stain on the enamel sample was measured by taking diffuse reflectance absorbance readings with a Minolta CM-503i Spectrophotometer (Minolta Camera Co., Ramsey, N.J.). Absorbance measurements over the entire visible color spectrum were obtained using the CIELAB color scale. This scale quantifies color according to 3 parameters, $L^*$ (lightness-darkness scale), $a^*$ (red-green chroma), and $b^*$ (yellow-blue chroma). An average of 3 absorbance readings using the $L^*a^*b^*$ scale were taken for each specimen. The overall change in the color of the stained enamel sample was calculated using the CIELAB equation: $\Delta E=[(\Delta L^*)^2+(\Delta a^*)^2+(\Delta b^*)^2]^{1/2}$. Stain removal is related to the $\Delta E$ or $\Delta L$ score after treatment. Increasing $\Delta E$ or $\Delta L$ scores indicate higher stain removal.

Table XXVII summarizes the average $\Delta E$ and average $\Delta L$ values for the flosses coated with the coating formulations of Table XXVI. The number of specimens used for each $\Delta E$ and $\Delta L$ reported below is 8 (n=8).

TABLE XXVII

| Formulation | Baking soda Mg/yd tape | Sident 10 silica Mg/yd tape | Zeodent silica Mg/yd tape | ΔL | ΔE |
|---|---|---|---|---|---|
| 9-1 | 0 | 0 | 0 | 0.55 | 0.95 |
| 9-2 | 0 | 4 | 0 | 3.03 | 3.54 |
| 9-3 | 1 | 3 | 0 | 2.78 | 3.18 |
| 9-4 | 2 | 2 | 0 | 3.05 | 3.59 |
| 9-5 | 2 | 0 | 0 | 3.48 | 4.17 |
| 9-6 | 3 | 1 | 0 | 2.13 | 2.65 |
| 9-7 | 4 | 0 | 0 | 0.69 | 1.00 |
| 9-8 | 1.4 | 1.4 | 0 | 1.56 | 1.83 |

Table XXVII shows that the floss with no coating (Formulation 9-1), or 10 w/w % baking soda (Formulation 9-7) show slight stain removal (ΔE of approximately 1). As the amount of Sident 10 silica is increased, stain removal increased. Surprisingly, formulation 9-4 showed the best stain removal of the flosses coated with Sident 10 silica. Formulation 9-5 showed the best stain removal of any tested formulation.

We claim:

1. An elastomeric monofilament dental tape, comprising:
a core body comprising a first cleaning surface and a second cleaning surface opposite said first cleaning surface, said core body having an aspect ratio of greater than 5:1;
a plurality of ribs, wherein said ribs are disposed along the entire length of each of said first and second cleaning surfaces, wherein the width of said dental tape is from 0.040 to 0.100 inches and the ratio of the width of said dental tape to the thickness of said dental tape is from 3:1 to 25:1; and
a substantially uniform coating comprising 0.8 milligram or more per yard dental tape of an abrasive selected from the group consisting of silica, di-calcium phosphate and alumina, and 0.8 milligram or more per yard dental tape of sodium bicarbonate.

2. The elastomeric dental tape of claim 1 wherein said ribs on said first cleaning surface are offset from said ribs on said second cleaning surface.

3. The elastomeric dental tape of claim 1, wherein said coating further comprises an ingredient selected from the group consisting of a lubricating agent, a release agent, a whitening agent selected from the group consisting of calcium peroxide, hydrogen peroxide, carbamide peroxide and other peroxide compounds capable of generating hydrogen peroxide in-situ, an active agent, an olfactory stimulant, a sialagogue, a sensate, an essential oil, a flavor, an antimicrobial agent and an anti-viral agent.

4. The elastomeric dental tape of claim 1 wherein said plurality of ribs comprises 10 ribs, wherein said ribs are disposed along the entire length of each of said first and said cleaning surfaces.

5. The elastomeric dental tape of claim 1 wherein the elastomeric material is selected from the group consisting of polyamide-polyether block copolymers, polyester-polyether block copolymers, polyester-polyester block copolymers, aliphatic thermoplastic polyurethane elastomers, aromatic thermoplastic polyurethane elastomers and thermoplastic polyolefin elastomers.

6. The elastomeric dental tape of claim 1 wherein said plurality of ribs comprises 8 ribs, wherein said ribs are disposed along the entire length of each of said first and said cleaning surfaces.

7. The elastomeric dental tape of claim of claim 6 wherein the ratio of the width of said dental tape to the thickness of said dental tape is from 10:1 to 20:1.

8. The elastomeric dental tape of claim 6 wherein the ribs have a cross-sectional configuration which is substantially rectangular and the ratio of the height of said ribs to the width of said ribs is from 1.5:1 to 8:1.

9. The elastomeric dental tape of claim 8 wherein the spacing between said ribs is substantially equal and wherein said ribs on said first cleaning surface are offset from said ribs on said second cleaning surface.

10. The elastomeric dental tape of claim 1 wherein said coating further comprises a microcrystalline wax, 1.4 milligram per yard dental tape or more of said sodium bicarbonate and 1.4 milligram per yard dental tape or more of said abrasive, wherein said abrasive comprises silica.

11. The elastomeric dental tape of claim 10 comprising 2 milligram per yard dental tape of said sodium bicarbonate and 2 milligram per yard dental tape of said abrasive, wherein said abrasive comprises silica.

12. The elastomeric dental tape of claim 1 comprising 2 milligram per yard dental tape of said sodium bicarbonate and 2 milligram per yard dental tape of said abrasive, wherein said abrasive comprises silica.

* * * * *